United States Patent [19]

Franz et al.

[11] Patent Number: 4,867,793
[45] Date of Patent: Sep. 19, 1989

[54] NACREOUS PIGMENTS

[75] Inventors: Klaus D. Franz, Kelkheim; Kalus Ambrosius, Frankfurt am Main; August Kanpp, Dieburg; Hans D. Brücker, Darmstadt, all of Fed. Rep. of Germany

[73] Assignee: Merck Patent Gesellschaft mit Beschränkter Haftung, Fed. Rep. of Germany

[21] Appl. No.: 52,822

[22] Filed: May 22, 1987

[30] Foreign Application Priority Data

May 23, 1986 [DE] Fed. Rep. of Germany ....... 3617430

[51] Int. Cl.$^4$ .............................................. C04B 14/20
[52] U.S. Cl. .................................... 106/415; 106/425; 106/436; 106/453; 106/456
[58] Field of Search ............... 106/415, 425, 436, 453, 106/456

[56] References Cited

U.S. PATENT DOCUMENTS

| | | | |
|---|---|---|---|
| 3,087,828 | 4/1963 | Linton | 106/291 |
| 3,331,699 | 7/1967 | Marshall et al. | 106/291 |
| 3,874,890 | 4/1975 | Bernhard et al. | 106/304 |
| 3,926,659 | 12/1975 | Bernhard et al. | 106/304 |
| 4,047,969 | 9/1977 | Armanini et al. | 106/304 |
| 4,075,384 | 2/1978 | Suzuki et al. | 106/304 |
| 4,146,403 | 3/1979 | Armanini et al. | 106/304 |
| 4,192,691 | 3/1980 | Armanini | 106/304 |
| 4,435,220 | 3/1984 | Watanabe et al. | 106/291 |
| 4,482,389 | 11/1984 | Franz et al. | 106/291 |
| 4,509,988 | 4/1985 | Bernhard | 106/308 R |
| 4,618,375 | 10/1986 | Patil et al. | 106/304 |

Primary Examiner—Paul Lieberman
Assistant Examiner—Willie J. Thompson
Attorney, Agent, or Firm—Millen, White & Zelano

[57] ABSTRACT

Platelet-shaped colored pigments in which a platelet-shaped substrate is provided with a compact coating containing iron(II) oxide, which coating has a high gloss and, depending on the layer thickness, shows the interference color of thin platelets, are described.

20 Claims, No Drawings

NACREOUS PIGMENTS

BACKGROUND OF THE INVENTION

The Application relates to platelet-shaped colored pigments in which a platelet-shaped substrate is covered with a layer containing iron oxide.

Colored platelet-shaped pigments containing iron oxide are known per se. In particular, layers of $Fe_2O_3$, if appropriate together with other metal oxides, such as, for example, $TiO_2$, are applied to platelet-shaped substrates, in particular mica. However, it is furthermore also known from German Offenlegungsschrift 2,313,331, which corresponds to U.S. Pat. No. 3,926,659, that layers containing iron(II) oxide can be deposited, uniform layers of magnetite on mica or on mica coated with metal oxides being produced by precipitation from iron-(II) salt solutions in the presence of an oxidizing agent. As explained in the third paragraph on page 7 of German Offenlegungsschrift 2,313,331, these are rough layers which show no interference colors and therefore also have no nacreous luster. Only if mica/metal oxide interference pigments are used as a substrate for a magnetite coating can this interference color still shine through in the case of very thin magnetite layers, but the magnetite layer itself is not capable of producing interference colors of thin platelets.

The same applies to the black pigments described in Example 8 of European Patent Application 0,077,959, which corresponds to U.S. Pat. No. 4,435,220, which are prepared analogously to the process of German Offenlegungsschrift 2,313,331, except that the precipitation of the magnetite is carried out in the presence of an alkaline earth metal salt with the aim of improved heat stability.

Although these known magnetite pigments can readily be used as platelet-shaped black pigments for many purposes, they cannot be referred to as nacreous pigments in the actual sense because of the lack of interference ability and a lack of luster.

SUMMARY OF THE INVENTION

It is therefore an object of this invention to provide platelet-shaped pigments which contain iron oxide and, in addition to the body color, additionally have a high gloss and can also display the interference color of thin platelets, depending on the thickness of the layer. It was an additional object to provide such pigments which are suitable for applications both in technology and in cosmetics.

Upon further study of the specification and appended claims, further objects and advantages of this invention will become apparent to those skilled in the art.

These objects have been achieved by the present invention. In particular, it has been found that uniform smooth layers which contain iron(II) oxide, have a high luster and impart to the pigment an attractive powder color, and if appropriate can produce the interference colors of thin platelets, can be produced on platelet-shaped substrates.

The application therefore relates to platelet-shaped colored pigments in which a platelet-shaped substrate is covered with a layer containing iron oxide, in which pigments the layer contains iron (II) oxide and is formed as a compact lustrous layer.

DETAILED DESCRIPTION

It has been found, surprisingly, that these layers which are capable of interference and contain iron oxide can be prepared both by wet chemistry, by direct precipitation of magnetite from iron (II) salt solutions in the presence of an oxidizing agent, and from $Fe_2O_3$-coated pigments by heating the pigments in the presence of a reducing gas. An essential feature of the preparation by wet chemistry is that, on contrast to the known processes, the oxidizing agent is not included in the suspension of the substrate to be coated, but both the iron(II) salt solution and the solution of the oxidizing agent are added simultaneously to the suspension.

The invention therefor also relates to a process for the preparation of colored platelet-shaped pigments containing iron oxide, which is characterized in that, to produce lustrous layers which can exhibit the interference colors of thin platelets, either an iron(II) salt solution and the solution of an oxidizing agent are simultaneously added to an aqueous suspension of a platelet-shaped substrate at substantially constant temperature and substantially constant pH and the pigment is separated off and, if appropriate, washed and dried, or a platelet-shaped substrate coated with a smooth homogeneous layer of $Fe_2O_3$ in a manner which is known per se is exposed to a reducing atmosphere at a temperature above 100° C.

The invention furthermore relates to the use of these pigments for pigmenting lacquers, paints, plastics and cosmetics.

In the context of the present invention, platelet-shaped pigments which contain iron(II) oxide and have a high gloss and the interference colors of thin platelets are rendered accessible for the first time. A critical factor in this is that the layer containing iron oxide on the new pigments consists of very much smaller and more densely packed primary particles than that of the known pigments. As can be seen from electron scanning microscopy (ESM) photographs, the primary magnetite particles in the known pigments, for example those prepared according to German Offenlegungsschrift 2,313,331 or European Offenlegungsschrist 0,077,959, are in the form of relatively coarse crystals of about 0.5 $\mu$m diameter distributed irregularly and with relatively large free intermediate spaces on the surface of the substrate.

In the pigments according to the invention, on the other hand, the primary particles are significantly smaller and, above all, also lie in closely packed distribution on the substrate.

The size of the primary particles is substantially less than 0.3 $\mu$m and, depending on the preparation process used, even in some cases significantly below 0.1 $\mu$m. However, it is critical that in each case the packing of the particles is so dense that the intermediate spaces between adjacent primary particles are as a rule smaller than the particle diameters. In any event, suitable states of compactness, smoothness and particle size oft the layers of this invention will include all of those which are effective to permit the mentioned interference effects when the layers are in contact with a platelet surface, e.g., mica, and are of sufficient thickness to be compatible with the underlying interference phenomena. Typically, at least 90% or more of the primary particles will have a diameter less than 0.3 microns an at least 90% or more of the intermediate spaces will have diameters less than the average size of the particles.

These properties are inherently achieved by the methods described herein.

The process for the preparation of these advantageous new pigments is also new. In this process, either a magnetite layer can be precipitated directly onto a suitable platelet-shaped substrate by wet chemistry, or the platelet-shaped substrate can first be coated with iron(III) oxide, which is then reduced to a layer containing iron(II) oxide.

Possible platelet-shaped substrates per se are all the platelet-shaped materials which are stable under the coating conditions, such as, for example, mica, glass platelets, metal platelets, graphite and other platelet-shaped materials.

Mica, such as, for example, muscovite or phlogopite, is preferably used. However, materials which already have a coating of metal oxide can also be used as the platelet-shaped substrate. In particular, mica platelets with one or more coatins of, for example, $TiO_2$, $ZrO_2$, $SnO_2$, $Cr_2O_3$, BiOCl, $Fe_2O_3$, $Al_2O_3$, $SiO_2$, ZnO or mixtures of these metal oxides can be employed as the platelet-shaped substrate.

The size of these platelet-shaped substrates is not critical per se and particles of a size suitable for the intended use can therefore be employed. As a rule, the substrate is employed in particle sizes of about 1 to 200 $\mu$m, in particular about 5 to 100 $\mu$m. The thickness of the particles is as a rule about 0.1 to 5 $\mu$m, in particular about 0.5 $\mu$m.

The starting materials used as substrates are known or can be prepared by known processes. Mica particles of the desired order of size can be obtained by grinding of mica and subsequent grading. Materials coated with metal oxide, in particular mica platelets coated with metal oxide, are both commercially available, for example from E. Merck, Darmstadt, as Iriodin® nacreous pigments, and able to be prepared by known processes. Such processes are described, for example, in the following patents and patent applications: U.S. 3,087,828, U.S. 3,087,829, DE 1,959,998, DE 2,009,566, DE 2,214,545, DE 2,244,298, DE 2,313,331, DE 2,522,572, DE 3,137,808, DE 3,137,809, DE 3,151,343, DE 3,151,354, DE 3,151,355, DE 3,211,602 and DE 3,235,017.

Depending on the preparation process and the substrate used, the layer containing iron(II) oxide can have various compositions. Thus, it is possible to apply a mangetite coating by wet chemistry. In contrast to the known processes, however, compact lustrous layers which also exhibit the interference color of thin platelets if the layer thickness is adequate are obtained by the process according to the invention.

If platelets coated with metal oxide are employed as the substrate, mixed phases can develop at the magnetite/metal oxide phase boundary. These mixed phases are also to be understood as mangetite layers in the context of the invention.

The layer containing iron(II) oxide can, however, also be present as a substantially pure layer of iron(II) oxide (wustite phase; $Fe_{0.90-0.95}O$) or as a mixed oxide with other metal oxides. Examples of such mixed oxides which may be mentioned are iron aluminate ($FeAl_2O_4$), chromite ($FeCr_2O_4$), iron orthosilicate ($FeSiO_4$) and, in particular, also ilmenite ($FeTiO_3$).

Both wustite and the mixed oxides with other metals are obtained, in particular, by reducing layers containing iron(III) oxide with a reducing gas at elevated temperature. Here also, other mixed phases may develop, especially at the phase interfaces, depending on the substrate used. These are also included in the definition, according to the invention, of layers containing iron(II) oxide. The relative amounts of iron(II) and other oxides are not critical and are determined by the desired effect achieved in the pigment. As a rule, these other oxides can be present in the iron(II)-containing layer in amounts of from 0–100 mole %.

For coating with magnetite by wet chemistry, the substrates are suspended in water and an iron(II) salt solution and an oxidizing agent are added as a suitable temperature and suitable pH. The suitable temperature range is about 0 to 100° C.; the reaction is preferably carried out at about 50° to 100° C. The pH of the suspension should be greater than 7; a pH between 8 and 11 is preferably established.

The addition of the iron(II) salt, such as, for example, ammonium iron(II) sulfate, iron(II) halides or, in particular, iron(II) sulfate, is carried out so that the iron oxide hydrate precipitated is deposited immediately on the substrate and no secondary precipitation occurs in the suspension. The pH is kept constant as far as possible during the precipitation. This is most advantageously effected by simultaneous addition of a base, such as, for example, NaOH, KOH or ammonia; however, it is also possible to use a suitable buffer system.

The precipitation of the iron oxide is carried out in the presence of an oxidizing agent, preferably a nitrate or a chlorate, which as far as possible is employed in a stoichiometric amount, that is to say in the case of a nitrate 1 mol of the nitrate is used for a maximum of 12 mol of iron(II) ions. It is critical that the oxidizing agent is not included in the suspension per se, as is the case in the processes of the prior art, but is metered into the suspension in the required stoichiometric amount at the same time as the iron(II) salt solution. Surprisingly, very smooth dense layers of $Fe_3O_4$ which, in contrast to those of the prior art, produce the interference colors of thin platelets are deposited. The ESM photographs clearly show that the magnetite layer consists of finely crystalline densely packed crystals with a size in the range from about 0.1 to 0.3 $\mu$m.

Depending on the desired effect, the layer containing iron oxide can be up to about 500 nm thick, preferably 0.1 to 250 nm thick. As a rule $Fe_3O_4$ contents which, based on the substrate, make up about 0.1 to 200% by weight, in particular 5 to 100% by weight, are achieved. Depending on the thickness of the magnetite layer, interference colors are achieved which pass from silver via gold, red, violet and blue to green and finally to interference colors of a higher order as the layer thickness increases.

When the desired interference color is reached, coating is interrupted and the coated substrate is as a rule separated off from the reaction mixture, washed with water and dried. To avoid undesirable oxidation, drying can be carried out, if appropriate, in an inert gas atmosphere, such as, for example, nitrogen, or even by admixing a reducing gas, such as, for example, hydrogen. Drying is as a rule carried out at temperatures of about 80° to 120° C., in particular in an $N_2/H_2$ atmosphere, but higher temperatures of up to 800° C. can also be used, additional sintering of the magnetite layer occurring.

In some cases it is advantageous additionally to provide a covering layer on the new pigments. Layers of colorless oxides, for example titanium dioxide, zirconium dioxide, aluminum oxide, antimony oxide, zinc oxide, silicon dioxide, magnesium oxide or tin dioxide, each of which can be applied by itself or as a mixture, are advantageously used for this in a known manner. Such a covering layer can be applied by customary methods to pigments which have already been dried, or more easily still before separation of the pigments from the precipitation solution. The covering layer is in general thinner than the layers applied according to the invention. A layer of aluminum oxide hydrate or aluminum oxide usually as the effect of additional stabilization, and in particular both in respect of mechanical properties and in respect of resistance to weathering. The layer thickness here is not particularly critical, since aluminum oxide hydrates and aluminum oxides have a relatively low refractive index. The methods for application of such layers are known and are described, for example, in German Offenlegungsschrift 1,467,468. The precipitation of the magnetite can also be carried out in the presence of an alkaline earth metal salt in accordance with the method of European Offenlegungsschrift 77,959, to improve the heat stability of the pigments.

Alternatively to the process by wet chemistry, a coating, according to the invention, containing iron(II) oxide can, however, also be achieved by reduction of a previously applied layer containing $Fe_2O_3$. Possible starting materials here are all the abovementioned substrates. These platelet-shaped materials can be coated with iron oxide or iron oxide hydrate in a known manner. Such processes are described, for example, in U.S. Pat. No. 3,087,828, U.S. Pat. No. 3,087,929, German Offenlegungsschrift 1,959,998, German Offenlegungsschrift 2,244,298, German Offenlegungsschrift 2,313,331, German Offenlegungsschrift 2,723,871, German Offenlegungsschrift 3,030,056 and German Offenlegungsschrift 3,237,264. Mica-based pigments coated with iron oxide are also commercially available. The pigments marketed by E. Merck, Darmstadt, with the tradename Iriodin ® 400, 500, 502, 504, 520, 522, 524 and 530 and the Mearl-Russet, Cloisonne-Busset, Bronze and Copper grades marketed by Mearl, USA, may be mentioned in particular.

Either the substrates coated with iron oxide or iron oxide hydrate by one of the known processes or the commercially obtainable pigments are then exposed to a reducing atmosphere at an elevated temperature above 100° C. Temperatures of about 200° to 1,000° C., preferably 400° to 800° C., are used in particular here. Possible reducing agents are in principle all the reducing gases. Examples which may be mentioned are hydrogen, carbon monoxide, methane and ammonia, hydrogen preferably being employed. These gases can be employed in the pure form, or diluted with an inert gas, such as, for example, nitrogen, argon, helium or steam. Mixtures which contain about 20 to 60% of the reducing gas are preferably used.

The conversion of $Fe_2O_3$ into iron(II) oxide, magnetite or mixed phases of iron(II) oxide with other metal oxides takes place at a rate depending on the temperature and the nature of the reducing gas or gas mixture. The thickness of the $Fe_2O_3$-containing layer to be reduced, and whether the entire layer is to be converted or only a thicker or thinner covering layer, are also critical for the duration of the reaction. The period can thus be varied within a very wide framework. However, the optimum reduction time can in all cases be determined by a few orienting experiments. As a rule, periods of about 0.25 to 2 hours are appropriate. The reduction can in principle be carried out in any oven to be charged with reducing gas. In order to be able to carry out the process continuously, a rotating tube oven is preferably employed. The nature of the layer containing iron(II) oxide produced can also be influenced by the temperature. Thus, pure $Fe_2O_3$ layers are predominantly converted into magnetite at a relatively low temperature, such as, for example, about 400°–500° C., whereas the wustite phase is formed at high temperatures of about 700°–900° C.

In the thermal treatment with a reducing gas the quality of the layer produced by reduction is primarily determined by the quality of the original $Fe_2O_3$-containing layer. Since it is possible to prepare very finely crystalline homogeneous, densely packed $Fe_2O_3$-containing coatings, it is in this way possible to obtain coatings of the same quality containing iron(II) oxide. Thus, for example, reduction of the commercially available Iriodin ® pigments of the abovementioned 500 series gives pigments which, when examined by RSM, reveal that the primary particles in the layer are only about 0.1 $\mu m$ and below in size. The reduction can also be carried out with non-annealed products containing $Fe_2O_3$. The layers containing iron(II) oxide which are obtained by reduction of compact $Fe_2O_3$ layers are therefore particularly lustrous and stable.

The new pigments represent a substantial enrichment of the art. The powder color which ranges from dark to black, and the interference color which can be produced as desired, result in extremely interesting effects which can be utilized for various applications, and in the case in particular of substrates which themselves already have an interference color, this can be intensified and varied, for example by an iron(II) oxide/titanium dioxide mixed phase (ilmenite) or a magnetite layer. Fields of application result both in cosmetics, where the pigments according to the invention are used, for example, in powders, ointments, emulsions, grease sticks and other agents in concentrations of as a rule between 0.1 and 80%, and in industry, for example for pigmenting paints, lacquers or plastics. The advantage of the pigments according to the invention when used in cosmetics is on the one hand that magnetite, for example, is permitted as a cosmetics pigment, and on the other hand that both an outstanding color gloss and a black body color can be delivered with a single pigment.

There are moreover also further fields of use for platelet-shaped iron oxides with the crystal structure of magnetite where the combination of their electromagnetic properties and their shape is utilized. The magnetic interactions lead to a very pronounced parallel orientation of the individual particles in coating materials. In comparison with conventional iron oxides, very much higher packing densities can consequently be achieved, which manifests itself, for example, in an increased anti-corrosive effect, in a good shielding from electromagnetic interference fields and in a high conductivity.

The ease of alignment of platelet-shaped magnetic particles in magnetic fields and their different light-scattering ability, depending on the orientation of the platelets relative to an incident beam of light, can be utilized for mangneto-optical displays. Utilization of the Faraday effect opens up use for magneto-optical memories to the platelet-shaped iron oxides according to the invention. Except as disclosed, all details of the starting materials, their preparation and the processes herein are conventional or readily determinable by one of ordinary skill in the art using only routine experimentation.

The pigments produced according to the invention may be employed analogously to conventional pigments in the uses indicated above, e.g., as disclosed in the references cited herein.

Within further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLES

Example 1

A solution of 600 g of $FeSO_4 \cdot 7 H_2O$ in 2,000 ml of water acidified with 50 ml of concentrated sulphuric acid and a solution of 150 g of $KNO_3$ in 2,1000 ml of water are metered simultaneously into a suspension of 100 g of potash mica of diameter 5 to 50 μm in 2,500 ml of water at 80° C. and a pH of 8 in the course of one hour, with vigorous stirring, the pH being kept constant by addition of 15% strength sodium hydroxide solution. The pigment with a blue-black lustre and a magnetite coating is then filtered off, washed and dried at 100° C. for 3 hours.

Example 2

The procedure followed is analogous to Example 1, but a solution of 350 g of $FeSO_4 \cdot 7 H_2O$ and a solution of 90 g of $KNO_3$ are metered in. A black-gold pigment with a magnetite coating is obtained.

Example 3

The procedure followed is analogous to Example 1, but a solution of 450 g of $FeSO_4 \cdot 7 H_2O$ and a solution of 112 g of $KNO_3$ are metered in. A black-red pigment with a magnetite coating is obtained.

Example 4

The procedure followed is analogous to Example 1, but a solution of 700 g of $FeSO_4 \cdot 7 H_2O$ and a solution of 175 g of $KNO_3$ are metered in. A black-green pigment with a magnetite coating is obtained.

Example 5

The procedure followed is analogous to Example 1, but a mica/$TGiO_2$ pigment with a red interference color, corresponding to Example 4 of German patent specification No. 1,467,468, is employed as the starting material and is coated using 250 g of $FeSO_4 \cdot 7 H_2O$ and 50 g of $KNO_3$ to give a black-green pigment.

Example 6

50 g of a mica/$Fe_2O_3$ pigment which has a red-brown luster and an iron oxide content of 43% by weight (prepared according to Example 1 b of German Offenlegungsschrift 2,313,331) are reacted with a 1:1 mixture of nitrogen and hydrogen at a flow rate of 100 l per hour in a 50 cm long flow tube at 800° C. for 0.5 hours. A platelet-shaped product which has an anthracite luster and shows the characteristic lines of FeO and mica in the Debye-Scherrer diagram immediately recorded is obtained.

Example 7

The procedure followed is analogous to Example 6, but instead of the calcined $Fe_2O_3$ mica pigment, the precursor which has been merely dried is employed. At a reduction temperature of 400° C., a product which has a black luster and a red interference color and shows the characteristic lines of $Fe_3O_4$ and mica in the Debye-Scherrer diagram is obtained.

Example 8

66 g of a pigment which has a coating of 6 g of $Fe_2O_3$ in the non-annealed form on 60 g of an annealed $TiO_2$/mica pigment with a blue interference color are reduced at 800° C. in the same flow tube as in Example 6. A pigment which has a deep dark-blue metallic luster and shows the characteristic lines of ilmenite $(FeTiO_3)_2$, $TiO_2$ and mica in the Debye-Scherrer diagram is obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A platelet-shaped nacreous pigment comprising a platelet-shaped substrate and coated thereon, a smooth and compact layer containing an amount of iron(II) oxide and having sufficient smoothness and compactness that when in contact with a this platelet, it is capable of producing interference colors.

2. A pigment according to claim 1, wherein the iron(II) oxide layer contains iron(II) oxide particles packed sufficiently densely that the distance between adjacent particles is generally smaller than the diameter of the particles.

3. A pigment according to claim 1, wherein the diameter of the particles in the iron(II) oxide layer generally does not exceed 0.3 μm.

4. A pigment according to claim 1, wherein the substrate is mica, a glass platelet, a metal platelet or graphite.

5. A pigment as to claim 1, wherein the substrate is mica coated with $TiO_2$, $ZrO_2$, $SnO_2$, $Cr_2O_3$, BiOCl, $Fe_2O_3$, $Al_2O_3$, $SiO_2$, ZnO or a mixture thereof.

6. A pigment according to claim 1, wherein the iron(II) oxide is a mixed oxide with an oxide of a di-, tri- or tetravalent metal.

7. A pigment as to claim 6, wherein the iron(II) oxide is substantially pure iron(II) oxide, $FeAl_2O_4$, $FeCr_2O_4$, $FeSiO_4$ or $FeTiO_3$.

8. A pigment as to claim 1, wherein the iron oxide layer is 0.1–250 nm in thickness.

9. A pigment as to claim 1, wherein the content of iron(II) oxide is 0.1–200% by weight based on the substrate.

10. A pigment of claim 1, wherein the iron(II) oxide is magnetite or the wustite phase.

11. A process for the preparation of a pigment of claim 1, comprising simultaneously adding an iron (II) salt solution and a separate solution of an oxidizing agent to an aqueous suspension of a platelet-shaped substrate under conditions which effect precipitation of an iron(II)-containing layer onto the substrate.

12. A process according to claim 11, wherein the temperature is 0–100° C. and the pH is greater than 7 and the temperature and pH are maintained substantially constant.

13. A process according to claim 11, wherein the iron(II) salt is ammonium iron(II) sulfate, an iron(II) halide or iron(II) sulfate.

14. A process according to claim 11, wherein iron oxide hydrate is deposited on the substrate without secondary precipitation occurring in the suspension.

15. A process according to claim 11, wherein the oxidizing agent is a nitrate or a chlorate.

16. A process according to claim 14, wherein the oxidizing agent is $KNO_3$.

17. A process for the preparation of a pigment of claim 1, comprising exposing a platelet-shaped substrate coated with a smooth homogeneous layer of $Fe_2O_3$ to a reducing atmosphere effective to convert Fe(III) to an effective amount of Fe(II).

18. A process according to claim 17, wherein the temperature is above 100° C.

19. A process according to claim 17, wherein the reducing atmosphere contains 20–60% of a reducing gas comprising hydrogen, carbon monoxide, methane or ammonia.

20. A pigment according to claim 1, wherein the content of iron(II) oxide is 5-200% by weight of the substrate.

* * * * *

UNITED STATES PATENT AND TRADEMARK OFFICE
CERTIFICATE OF CORRECTION

PATENT NO. : 4,867,793
DATED : September 19, 1989
INVENTOR(S) : KLAUS D. FRANZ ET AL It is certified that error appears in the above-identified patent and that said Letters Patent is hereby corrected as shown below: On the title page:

Title page, second inventor's name:

reads "Kalus Ambrosius"

should read -- Klaus Ambrosius --

Title page, third inventor's name:

reads "August Kanpp"

should read -- August Knapp --

Title page, fourth inventor's name:

reads "Hans D. Brücker"

should read -- Hans D. Brückner --

Signed and Sealed this

Fourteenth Day of August, 1990

Attest:

HARRY F. MANBECK, JR.

*Attesting Officer*      *Commissioner of Patents and Trademarks*